United States Patent [19]
Spear et al.

[11] Patent Number: 5,883,389
[45] Date of Patent: Mar. 16, 1999

[54] DISTINGUISHING NATURAL FROM SYNTHETIC DIAMONDS

[76] Inventors: Paul Martyn Spear, 70 Portlock Road, Maidenhead, Berkshire, SL6 6DZ; Christopher Mark Welbourn, Still Bridge Cottage, West End, Waltham St. Lawrence Berkshire, RG10 0NT, both of England

[21] Appl. No.: 522,319
[22] PCT Filed: Apr. 3, 1994
[86] PCT No.: PCT/GB94/00415
§ 371 Date: May 29, 1996
§ 102(e) Date: May 29, 1996
[87] PCT Pub. No.: WO94/20837
PCT Pub. Date: Sep. 15, 1994

[30] Foreign Application Priority Data

Mar. 5, 1993 [GB] United Kingdom .................. 9304505
Mar. 5, 1993 [GB] United Kingdom .................. 9304506

[51] Int. Cl.$^6$ .................................................. G01N 21/87
[52] U.S. Cl. .......................................... 250/461.1; 356/30
[58] Field of Search ............................. 250/461.1; 356/30

[56] References Cited

U.S. PATENT DOCUMENTS

| 4,394,580 | 7/1983 | Gielisse . |
| 5,118,181 | 6/1992 | Yifrach et al. . |

FOREIGN PATENT DOCUMENTS

| 0071462 | 2/1983 | European Pat. Off. . |
| 0425426 | 5/1991 | European Pat. Off. . |
| 2 215 041 | 9/1989 | United Kingdom ..................... 356/30 |
| 2267147 | 11/1993 | United Kingdom . |
| 8300389 | 2/1983 | WIPO . |

OTHER PUBLICATIONS

Antwerp Facets, Oct. 1993, p. 25, Report International Diamond Manufacturers Association.
Antwerp Gems, 1993, vol. 4, No. 2 pp. 31–33, 26th World Diamond Congress; Resolution Concerning Compulsory Disclosure ect . . .
Anderson & Jobbins "Gem Testing", 10th Edition, Butterworths, pp. 125 and 202 to 205. (No Date).
Burns et al., "Growth–Sector Dependence of Optical Features in Large Synthetic Diamonds", Journal of Crystal Growth, vol. 104 (1990), pp. 257 to 279.
Davies, "The Optical Properties of Diamonds" vol. 13 (1977), pp. 56 and 57.
Marshall, "Cathodoluminescence of Geological Materials" Unwin Hyman, 1988 (only p. 21 available).
Partlow et al., "Cryogenic Cathodoluminescence of Plasma–Deposited Polycrystalline Diamond Coatings", Journal of Applied Physics, vol. 67, No. 11, 1990, pp. 7019 to 7025.
Ponahlo, "Quantitative Cathodoluminescence—A Modern Approach to Gemstone Recognition", Journal of Gemmology, vol. 21, (1988), pp. 182–193.
Ponahlo, "Cathodoluminescence (CL) and CL Spectra of DeBeer's Experimental Synthetic Diamonds", Journal of Gemmology, vol. 23, (1992), pp. 3 to 17.
Rooney et al., "DeBeers Near Colorless–To–Blue Experimental Gem–Quality Synthetic Diamonds", Gems & Gemmology, Spring 1993, pp. 38 to 45. (published May 20, 1993).
Shigley et al., "The Gemological Properties of the De Beers Gem–Quality Synthetic Diamonds", Gems and Gemmology, vol. 23, (1987), pp. 187–206.

*Primary Examiner*—Constantine Hannaher

[57] ABSTRACT

In order to provide a method of distinguishing natural from synthetic diamond which does not involve costly equipment or long periods to make a measurement, a diamond is irradiated with ultraviolet radiation which is preponderantly of wavelength 225 nm or less, such that substantially only the surface region of the diamond is irradiated. By observing the pattern or luminescence and/or phosphorescence produced by the diamond, an observer can identify the diamond as a natural or synthetic diamond.

17 Claims, 6 Drawing Sheets

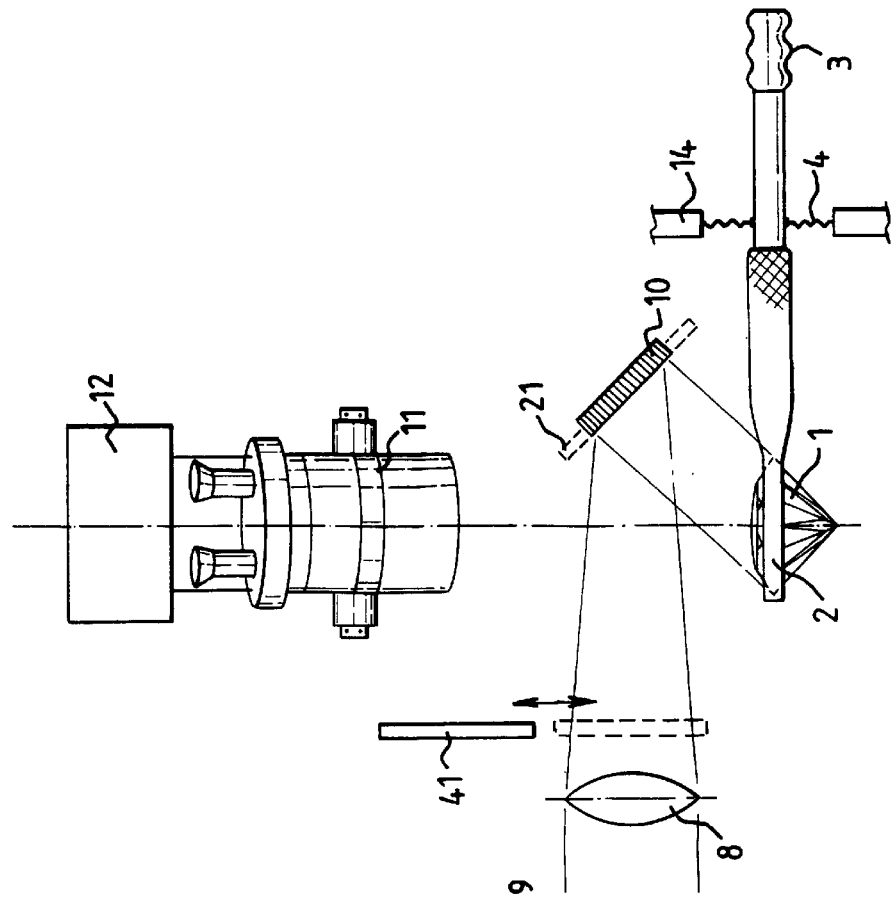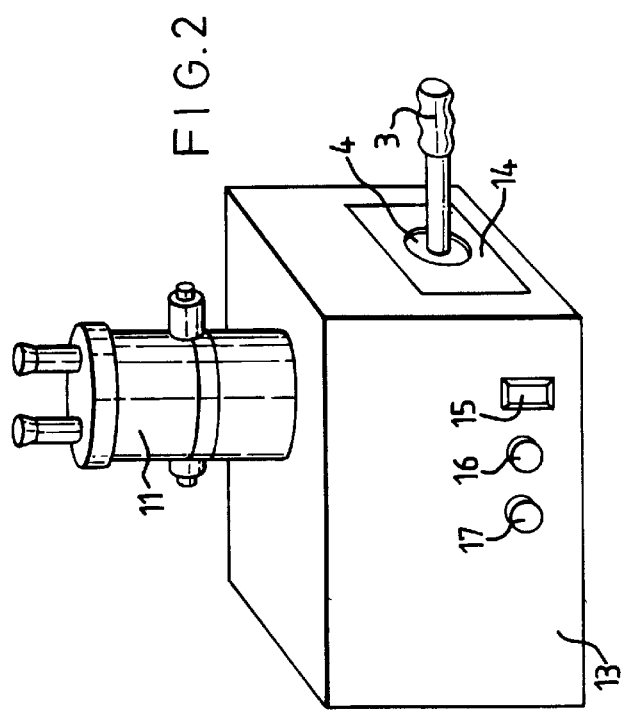
FIG. 1
FIG. 2

DISTINGUISHING NATURAL FROM SYNTHETIC DIAMONDS

BACKGROUND OF THE INVENTION

This invention relates to a method and apparatus for distinguishing natural diamond from synthetic diamond by observing the luminescence, for example by investigating the arrangement of growth sectors in the diamond.

Synthetic diamonds differ from natural diamonds in that synthetic diamonds show mixed habit growth, having different growth sectors through the body of the crystal. These different growth sectors all incorporate impurities as they grow, but do so at different rates and in different ways, and this gives them different spectroscopic properties. In an unpolished stone, the presence of different growth sectors in synthetic diamonds will produce characteristic growth faces on the surface of the diamond quite distinct from those formed on the surface of a natural diamond, which will tend to exhibit single habit octahedral growth. A skilled person can identify an unpolished synthetic diamond from a natural diamond just by looking at it, but all this surface information is removed if the stone is polished.

A technique known as cathodoluminescence has been developed and discussed in Woods & Lang (J. Crystal Growth vol 28 (1975) page 215), Burns et al (J. Crystal Growth vol 104 (1990) page 257), Shigley et al (Gems and Gemology, vol 23 (1987) page 187), and Marshall ("Cathodoluminescence of Geological Materials", 1988, published by Unwin Hyman, pages 19 to 36). This technique involves subjecting a diamond to an electron beam in an evacuated cathode ray chamber. With a typical energy of 18 keV, electrons will penetrate and cause excitation in a surface region to a depth of about 3 $\mu$m. Luminescence known as cathodoluminescence will be generated in this region. An image of the surface being excited can be then formed, this image showing the cathodoluminescence pattern.

Ponahlo (J. Gemology, vol 21 (1988) page 182) describes the use of the cathodoluminescence technique for distinguishing natural from synthetic emeralds and rubies.

The cathodoluminescence technique has significant disadvantages in the form of the apparatus required. The gemstone has to be placed in a vacuum chamber, which is expensive and increases the time required to make a measurement, and the electron beam generates X-rays which have to be screened. In addition, the cathode ray apparatus itself is expensive.

It is desirable to provide a method of distinguishing natural diamond from synthetic diamond without using complex and expensive apparatus or vacuum chambers.

Shigley et al discloses a method of short wave ultraviolet illumination of synthetic diamonds to study growth sectors, using ultraviolet radiation of a wavelength of 254 nm. This causes excitation into impurity energy level(s) specific to the particular type of diamond being studied. The technique described in this disclosure will only work with those diamonds that have a strong extrinsic absorption at 254 nm.

It is desirable to provide an observation technique that will work with a single wavelength or single band of wavelengths for all diamonds.

A paper by Walsh et al (Journal Of Luminescence, Volume 4 (1971) page 369) describes the thermoluminescence technique in natural and synthetic semi-conducting diamonds, and relates it to phosphorescence phenomena. Thermoluminescence is the thermal generation of luminescence following excitation at a low temperature, for example 77K. The sample is excited using an electron beam or photo-excitation from an arc lamp.

Upon raising the temperature of the sample, thermoluminescence peaks at different temperatures are observed. Phosphorescence may also be observed.

Phosphorescence is the decay of stimulated luminescence, following the removal of the excitation source, over a period of milliseconds to tens of seconds and sometimes over a period of minutes.

Thermoluminescence apparatus is complicated and expensive and may not be suitable for differentiating synthetic diamonds and natural diamonds.

THE INVENTION

The invention provides a method and apparatus for distinguishing natural from synthetic diamond.

Using the invention, it is possible to determine for most diamonds whether the diamond is natural or synthetic, employing apparatus which can be portable and can be of a cost and size which make it usable in say small-scale gemological laboratories, jewellery wholesale manufacturers and large jeweller retail establishments. Although ultraviolet of a wavelength less than 225 nm is dangerous to the eyes and skin if it escapes, complete shielding can be provided. Although normal optics cannot be used for delivering the ultraviolet to the sample, as they would attenuate and absorb the ultraviolet of a wavelength less than 225 nm, it is possible to provide special optics which do not grossly attenuate the ultraviolet.

The diamond is observed under ultraviolet excitation of such a wavelength that the surface structure can be distinguished, possibly with the assistance of the different colors of luminescence produced by different diamonds. A permanent image or surface topograph of the diamond can be formed, preferably magnified; however the method is preferably operated by observing the diamond by eye through a microscope. Once the eye has accomodated itself to a low light level, a good image is seen.

Ultraviolet radiation of wavelengths shorter than 225 nm interacts strongly with all types of diamond to cause luminescence, and thus the method and apparatus of the invention are suitable for use with any form of diamond. The luminescence bands observed for various types of diamond (natural or synthetic) fall within a wide range of wavelengths, generally in the visible part of the spectrum. For instance, one can identify patterns indicating the disposition of growth sectors in the diamond and hence the types of growth sectors present. Sectors of different growth type will luminesce with different colors, and may thus be distinguished. Growth sectors of the same type will have the same luminescence colour but may show different intensities. In this way, natural diamond can be distinguished from synthetic diamond as synthetic diamonds will in general show more than one type of growth sector. The method can also enable one to detect a surface deposition of synthetic diamond on a natural diamond. The invention is particularly useful for examining worked stones, i.e. fully polished or part-polished stones.

If it is difficult to distinguish natural diamond from synthetic diamond by looking at the growth sectors, particularly if there is only a single growth sector which gives little topographical information, the color can usually enable the observer to identify whether the diamond is natural or synthetic.

General luminescence microscopy is the technique of illuminating a diamond with ultraviolet light and observing through a microscope the characteristics of the stimulated luminescence from the bulk of the sample diamond, the whole of the diamond being excited. General luminescence microscopy is not suitable for studying the geometrical forms of the luminescence; even if a limited plane is focused upon, the rest of the luminescence severely reduces the contrast. If a composite image for the whole diamond were generated, the image would be very hard to interpret. However, the success of such a technique would be determined by the type of diamond material and strength of the bands emitted, and would vary from diamond to diamond.

In the invention, the exciting radiation does not penetrate very deeply into the crystal and substantially only the surface region is penetrated and irradiated. In this way, the surface region of the diamond may be observed. Luminescence emitted by regions of the diamond which are deeper than the surface region must be insufficient to render indistinct the luminescence produced by the surface regions; in other words that irradiating radiation which induces luminescence must be substantially absorbed in the surface region.

The degree of attenuation of the ultraviolet radiation within the diamond and hence the irradiated depth is dependent on the coefficient of absorption of the diamond at the irradiating wavelength; the attenuation follows an inverse exponential behavior with depth. When using radiation of a wavelength longer than 225 nm, for certain types of diamonds the absorption is not as strong as at 225 nm and the depth of diamond illuminated is much greater. The actual depth of diamond illuminated at a wavelength longer than 225 nm depends on the magnitude of the extrinsic defect (nitrogen) induced absorption at the exciting wavelength, which will vary considerably between diamonds. Thus, the induced luminescence may be generated all through the body of the crystal (which will be the case if the absorption is sufficiently weak) and the contrast of the images produced at the surface may be swamped.

At wavelengths less than about 225 nm, the absorption coefficient of all types of diamond is very high and the absorption coefficient of diamond increases rapidly with decreasing wavelength. In the absence of absorption from impurities, the absorption coefficient at about 225 nm is about 50 cm$^{-1}$ and at 223 nm it is greater than 400 cm$^{-1}$. The limit of absorption spectroscopy is achieved at about 208 nm with an absorption coefficient of about 5000 cm$^{-1}$—below about 208 nm, the absorption coefficient is too large to be measured. The "attenuation depth" at a given wavelength is the depth at which the radiation has been attenuated to about 13% of its incident intensity. This is given by 2/A, where A is the absorption coefficient at a given wavelength. From 225 nm to 208 nm the attenuation depth has decreased from 400 $\mu$m to 4 $\mu$m, being 50 $\mu$m at 223 nm. In general, in all diamonds, using a suitable filter allowing only radiation with wavelengths below 225 nm to be incident on the diamond, most of the radiation would be substantially absorbed within a depth of about 50 $\mu$m of the surface of the diamond—more specifically, the effective penetration depth for a uniform intensity distribution from 225 nm to 190 nm is substantially less than 50 $\mu$m. Thus the surface region can be considered to have a depth of about 50 $\mu$m, it being preferred that the irradiating ultraviolet radiation of a wavelength down to 190 nm, be attenuated to about 13% of the incident intensity (i.e. integrated over wavelength) within this depth; this depth is satisfactory provided that the intensity of any illumination having wavelengths above 223 nm or 225 nm is insignificant at a depth of not many times, e.g. three or four times, greater than 50 $\mu$m. Ideally, most of the irradiating radiation should be of a wavelength just slightly less than 225 nm.

To avoid excessive luminescence from deeper regions, the irradiating source should not contain any high intensity visible radiation (radiation above 380 nm) that could be transmitted to the body of the diamond to cause luminescence. Moreover, the absence of visible excitation means that there would be no contamination of the luminescence produced in the surface regions from scattered visible excitation light. Ideally, the radiation should be confined to ultraviolet radiation below 225 nm. Nonetheless, in practical embodiments some radiation of over 225 nm is permitted and as a general statement, the intensity of the irradiating radiation above 225 nm and up to 380 nm (the limit of visible radiation) is preferably not more than about 50% or about 25% or about 15% or about 10% or about 5% of the irradiating ultraviolet radiation below 225 nm. The oxygen in air cuts off radiation below about 180 nm and ultraviolet optics usually cut off radiation below about 180 or 190 nm. Thus, in considering the radiation above 225 nm and up to 380 nm as a percentage of the ultraviolet radiation below 225 nm, radiation below say 190 nm can be ignored.

Natural diamond can be distinguished from certain types of synthetic diamond merely by irradiating as set forth above, terminating the irradiation, and observing the phosphorescence. In general, merely observing the phosphorescence will not identify a number of different types of diamond, and this technique is preferably used as a step additional to that of observing the luminescence, when it can provide additional discrimination.

The phosphorescence is found to originate only from certain growth sectors in synthetic diamonds and lasts long enough to be observed, for up to several minutes. Phosphorescence in natural diamonds is a rare phenomenon and is almost exclusively found in diamonds of type IIb character, which contain an excess concentration of boron over nitrogen impurities. These diamonds are generally blue in color and have semi-conducting properties. On the other hand, phosphorescence is a common phenomenon in synthetic diamonds having a low nitrogen concentration, including those which are colorless or near colorless and those doped with boron to produce a blue color. Stones are either identified as natural (no phosphorescence) or are referred for further testing (phosphorescence). Although the technique cannot distinguish between natural and synthetic blue colored diamonds, natural blue diamonds are very rare so that only a small number of natural stones will be referred for further testing.

Observing the phosphorescence is useful in two ways;
i) In the absence of any growth sectorial information, if emissions persist for a perceptible time after removing the exciting ultraviolet radiation, the diamond should be suspected as being of synthetic origin;
ii) If the growth sectors are poorly defined due to the luminescence emissions being of a similar color, the contrast between the sectors may be enhanced when the ultraviolet radiation is removed; those growth sectors which do not phosphoresce will appear black.

It has been found that the observation of the luminescence caused by the ultraviolet enables one to detect a layer of synthetic diamond deposited upon the stone. This method is suitable for detecting synthetic diamond deposited on natural diamond, and is suitable for worked and especially fully polished stones.

In all cases, the intensity of the irradiation must be sufficient to obtain observable luminescence.

The invention will be further described by way of example and with reference to the accompanying drawings, in which:

BRIEF DESCRIPTION OF THE DRAWINGS

FIG. 1 shows the components of an ultraviolet photoluminescence topography apparatus according to the invention, and shows a possible modification;

FIG. 2 is an isometric projection of the apparatus of FIG. 1;

PREFERRED EMBODIMENTS

FIGS. 1 and 2

Figure 3:
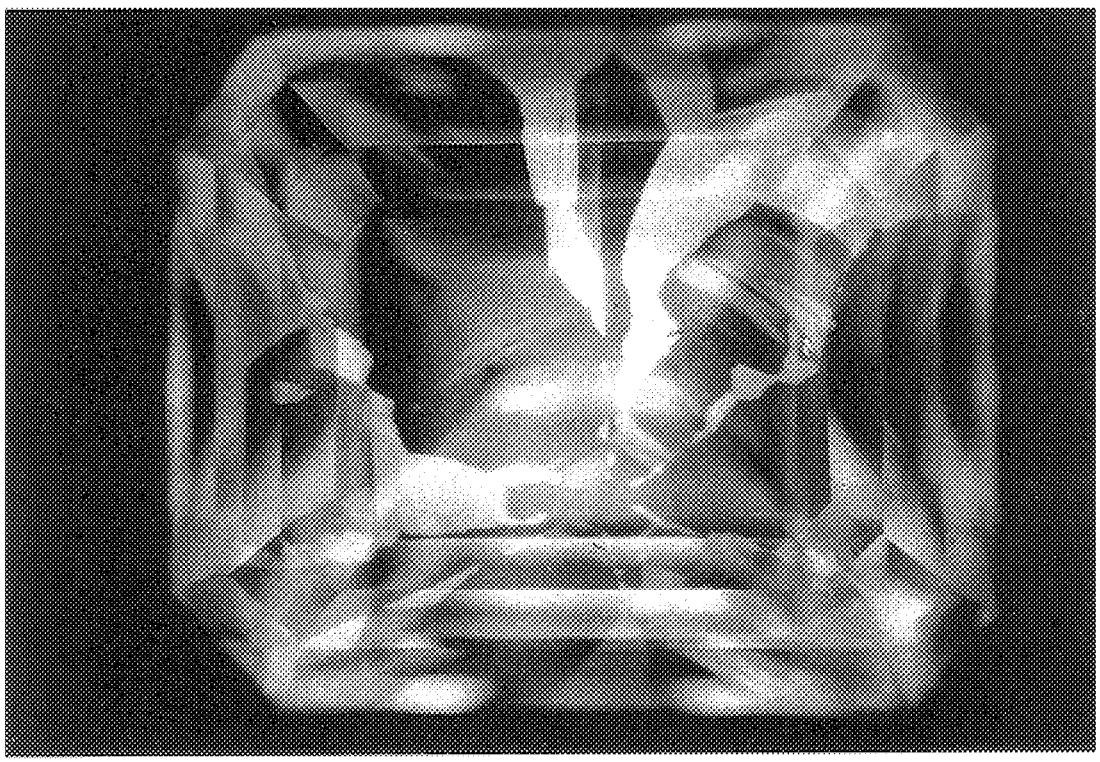
FIGS. 3 and 4 are examples of ultraviolet photoluminescence topographs of synthetic diamonds, obtained using the method and apparatus of the invention.

FIG. 1 shows the layout of apparatus for ultraviolet photoluminescence topography according to the invention. A polished diamond 1 is mounted in mounting means 2. The diamond 1 and mounting means 2 are shown to a larger scale than the rest of the apparatus. Any suitable mounting means 2 can be used, such as spring-loaded tweezers, vacuum tweezers or a conical depression. The mounting means 2 shown, purely as an example, are spring-loaded tweezers with rubber pads for gripping the diamond 1 and a protruding handle 3 for manipulation of the diamond 1, with a rubber bellows 4 for ultraviolet shielding. The girdle of the diamond 1 can be gripped (as shown) for some views, and the table and culet point gripped for other views.

The diamond 1 is illuminated with short wavelength (225 nm or less) ultraviolet radiation produced by a light source 5. A water-cooled Hamamatsu 150 W deuterium light source may be used, but the preferred source is a UV rich xenon flash lamp, which contains all wavelengths from 190 nm to beyond 1000 nm. The preferred xenon lamp illumination system consists of the xenon lamp unit 5, which comprises a xenon lamp, a capacitor and a trigger transformer, and a power supply unit 6. The capacitor is connected across the lamp and is charged to a defined voltage by the power supply unit. In response to a signal from the signal generator, the power supply unit provides a trigger pulse to the trigger transformer, which is connected to the lamp, and initiates the flash. A suitable illumination system consists of a PS-450AC power supply, used with an integrated trigger transformer and lamp base FYD 506 Lite Pac, a CP-1229 1 $\mu$P, 600 V capacitor and an FX-504U xenon flash lamp, all supplied by EG&G Electro-Optics of Salem, Mass., USA. The lamp has a maximum mean operating power of 20 W and is operated at a frequency of 50 to 200 Hz, and increase in frequency causing an increase in effective intensity. The signal generator can be any suitable TTL square wave generator, one suitable generator being a Levell function generator type TG 301, supplied by Digitron Instruments Ltd, of Hartford, Great Britain.

The beam of light from the light source 5 is focused by 25 mm focal length ultraviolet grade quartz lenses 7 and 8, and a cut-on interference filter 9 is provided. The filter 9 may be for instance an Omega 200 nm ultraviolet transmission filter, but is preferably a G25 206F filter supplied by the Corion Corp. of Holliston, Mass., USA, which has a peak transmission at 206 nm; having regard to the spectral output of the lamp 5, the intensity of the ultraviolet radiation transmitted by the Corion filter 9 above 225 nm (up to 380 nm) is about 4% of the ultraviolet radiation transmitted between 190 nm and 225 nm, i.e. the radiation transmitted is preponderantly or substantially of a wavelength of less than 225 nm.

A steerable ultraviolet grade mirror 10 is provided to direct the light onto the surface of the diamond 1. An image of the photo-luminescence patterns produced on the surface of the diamond being studied is produced and studied by eye using magnifying means in the form of a microscope 11 in the preferred embodiment, but a camera or CCD image recorder 12 (shown schematically) may be provided for later study or processing of the results. The glass of the microscope optics cuts out any hard ultraviolet radiation, say that having a wave length of less than 300 to 330 nm, and very little ultraviolet radiation would in any case pass up through the microscope 11. Any suitable microscope 11 may be used, preferably having a microscope ocular with a zoom attachment, and the microscope 11 may be a standard gemological microscope with a facility or camera 12 to record the image on fast film. Color film can be used.

FIG. 2 shows just by way of example the apparatus contained in a casing 13 to provide ultraviolet shielding, the mounting means 2 being in a sliding drawer 14 with suitable rubber seals for shielding. Controls 15, 16, 17 are shown schematically for power supply on/off, power supply frequency and mirror steering. The apparatus may be constructed so that it is portable and occupies a fairly small space, to provide a handy and portable device for distinguishing natural diamonds and synthetic diamonds. For example, the signal generator and power supply 6 for the light source 5 may occupy a space of only 215 mm×310 mm×110 mm and the length, breadth and height of the casing 12 can be about 500 mm×250 mm×250 mm. However, it is believed that these casing dimensions can be reduced to say 300 mm×200 mm×200 mm.

A skilled operator observing a polished diamond 1 using the apparatus of FIG. 1 would look for geometric patterns indicating mixed habit growth, which indicate synthetic diamond.

As an example, a 1 ct. (0.2 g) circular brilliant-cut diamond 1 can be examined using the EG&G xenon lamp 5 using a 200 Hz frequency. For examination by eye, the signal generator is left on long enough to complete the examination. For making a photographic topograph, the signal generator can be left on several minutes, depending on the photographic film used and the aperture. For recording using a CCD image recorder 12, a few seconds may be sufficient.

The transmission filter 9 and the ultraviolet grade mirror 10 can be replaced by a single dichroic fused silica steerable reflection filter 21. The reflection filter 21 can be inserted in the same position as the mirror 10. The transmission characteristic of this filter 21 shows it to have a peak front surface reflection at about 200 nm. There is on average about 2% reflection at wavelengths greater than 225 nm and the intensity of radiation reflected in the range 225–380 nm is about 20% of the ultraviolet radiation reflected between 190 nm and 225 nm. Accordingly, a wavelength band in which substantially or preponderantly all wavelengths are less than 225 nm can be projected on to the diamond 1. The emitted photoluminescence is transmitted by the filter 21 to the microscope 11. An anti-reflection coating on the back surface of the filter 21 for visible wavelengths of 400 to 700 nm enhances the transmission.

FIGS. 3, 3a, 4, 4a, 5, 5a, 6, 6a and 7

FIGS. 3, 4, 5 and 6 show examples of ultraviolet photoluminescence surface topographs for synthetic and natural diamonds, to illustrate the kind of results achieved.

Figure 4:
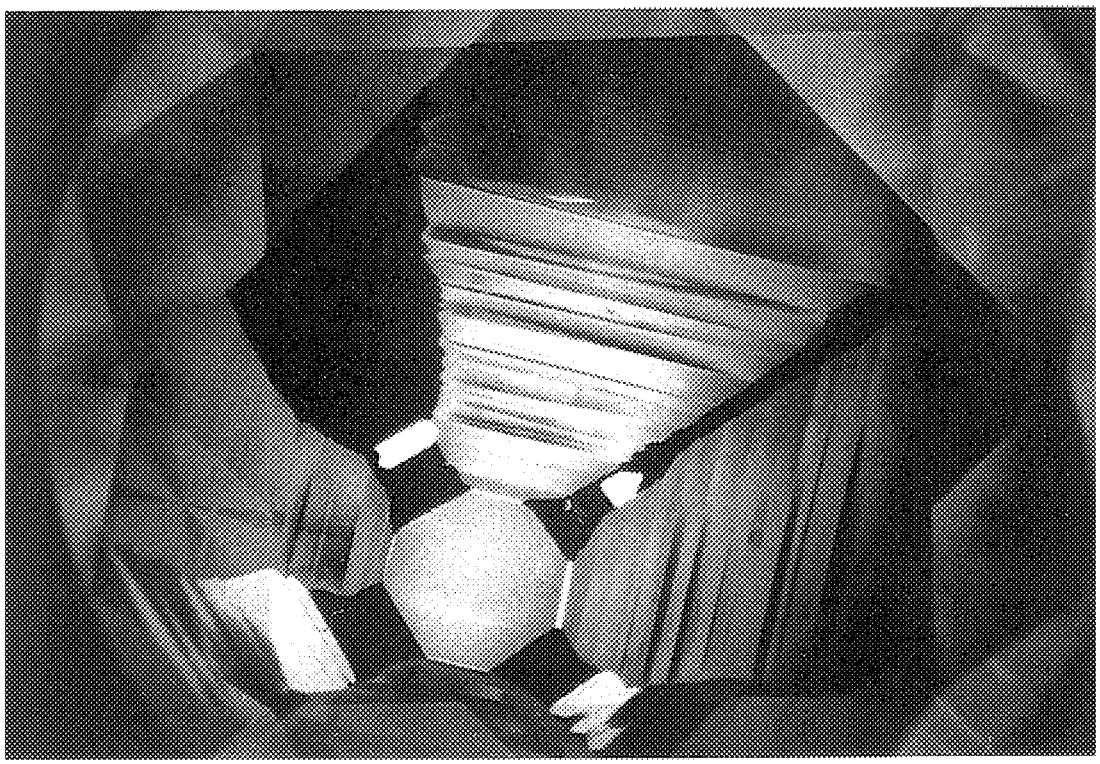
Figure 3A:
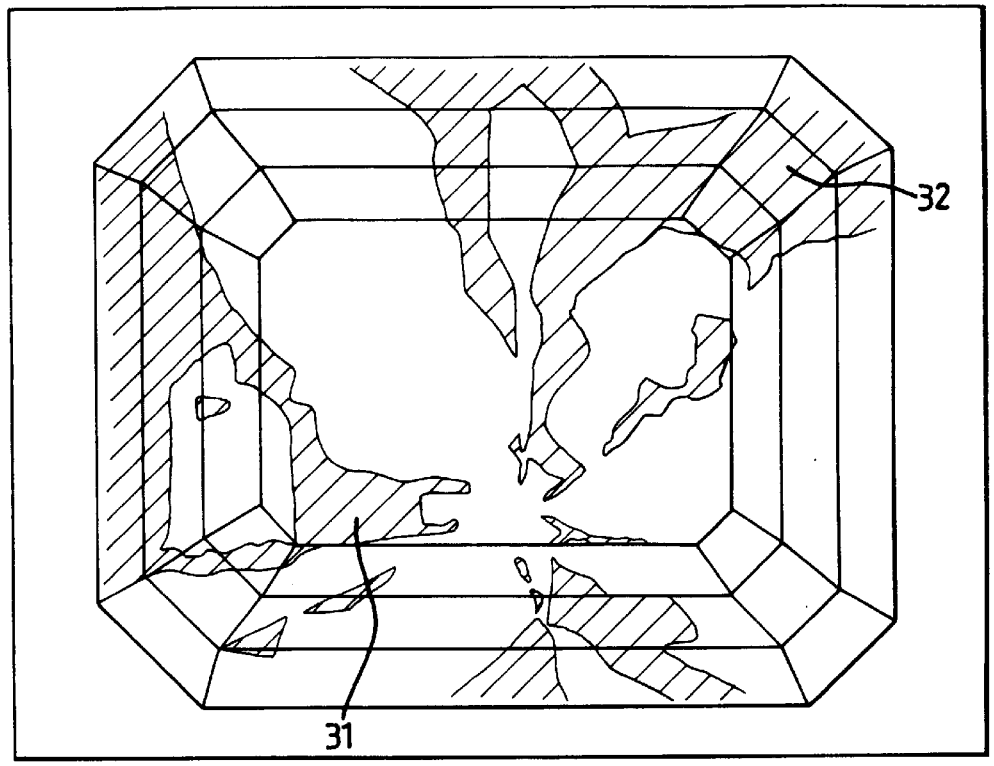
FIGS. 3a and 4a are diagrammatic representations of the major features of FIGS. 3 and 4.
Figure 4A:
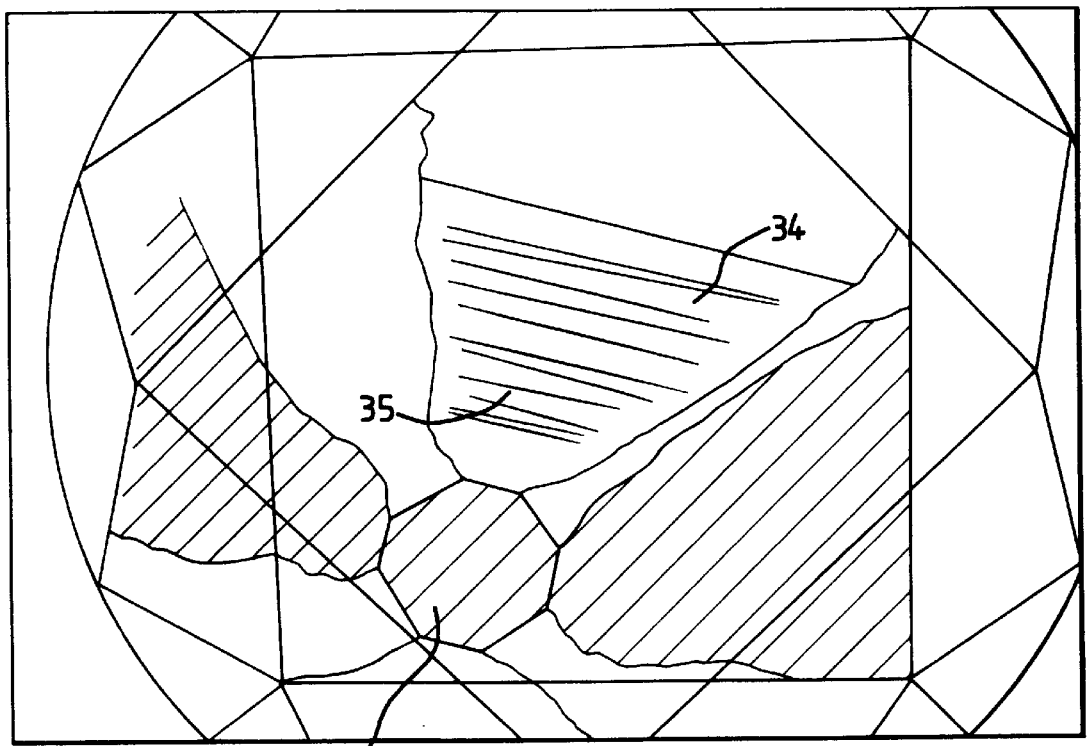

FIGS. 3 and 4 are views of the table of an emerald-cut synthetic diamond and the table of a circular brilliant-cut synthetic diamond, respectively, only part of the stone being shown in FIG. 4. The photoluminescence of the synthetic stone shown in FIG. 3 was essentially pale blue and showed colored banding; that of the synthetic stone shown in FIG. 4 was predimnantly yellow in color, though with regions of blue, and showed yellow and green banding. Regions 31, 32, 33, 34 are identified in FIG. 3a (representing the major features of FIG. 3) and FIG. 4a (representing the major features of FIG. 4), showing different growth sectors, the striated portions 35 in FIG. 4a being due to growth banding. Both of these views show characteristic mixed-habit growth of synthetic diamonds.

Figure 5:
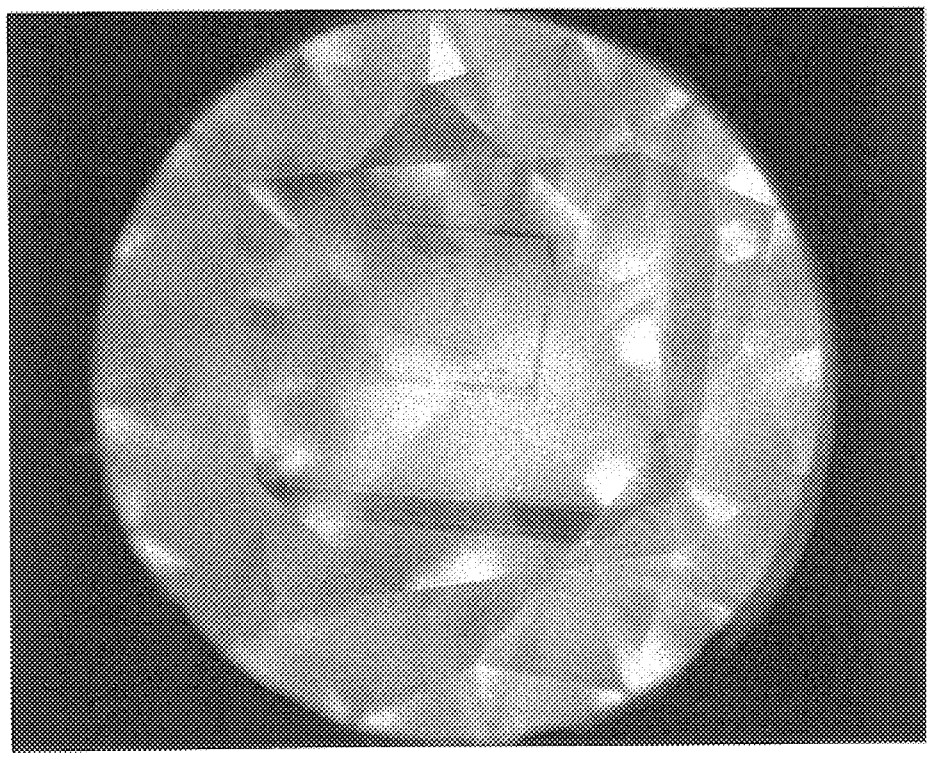
FIGS. 5 and 6 are examples of ultraviolet photoluminescence topographs of natural diamonds, obtained using the method and apparatus of the invention.
Figure 6:
Figure 5A:
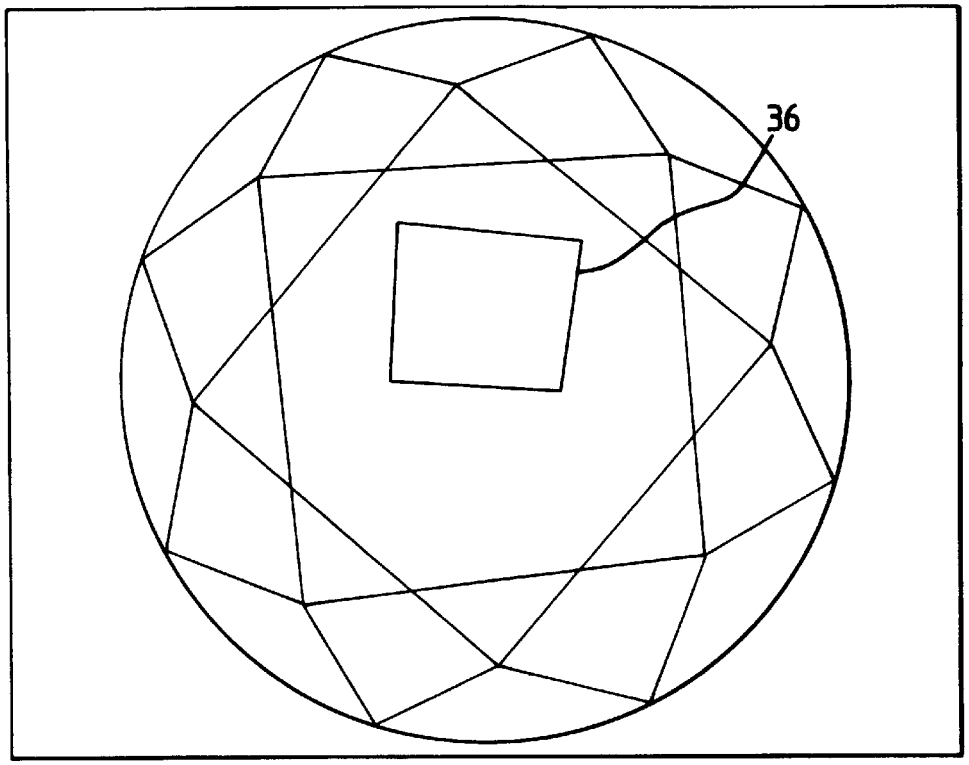
FIGS. 5a and 6a show diagrammatic representations of the major features of FIGS. 5 and 6.

FIGS. 5 and 6 are views of the tables of two circular brilliant-cut natural diamonds taken under identical conditions to FIGS. 3 and 4. The natural stones of FIGS. 5 and 6 were blue in photoluminescence, which is typical for natural stones. Most natural diamonds are type Ia and emit blue luminescence due in part to a band commencing at 415 nm (N3 band) and extending to longer wavelengths. This band is almost coincident with the blue bands emitted by natural and synthetic type IIb semi-conducting diamonds. Natural type IIa diamonds (containing very low point defect concentrations) tend to luminesce very weakly under ultraviolet excitation at 225 nm or less.

Figure 6A:
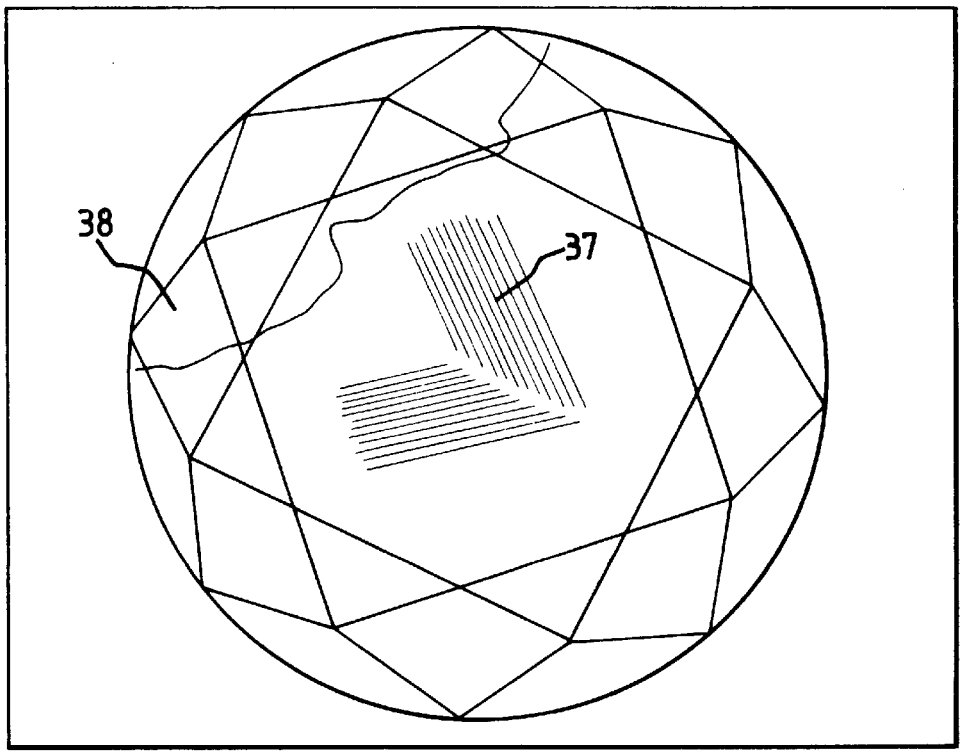

The patterns on the images of the natural stones are almost entirely formed by the cut of the crystal and there is very little distinct banding. A distorted square 36 is identified in FIG. 5a but this is the only evidence of growth banding. FIG. 6a shows some growth banding 37 near the center of the table only. A person skilled in the art studying these diamonds would recognize the octahedral growth only. The bright area 38 in the corner of FIG. 6a is due to light scattering from an internal crack.

Figure 7:
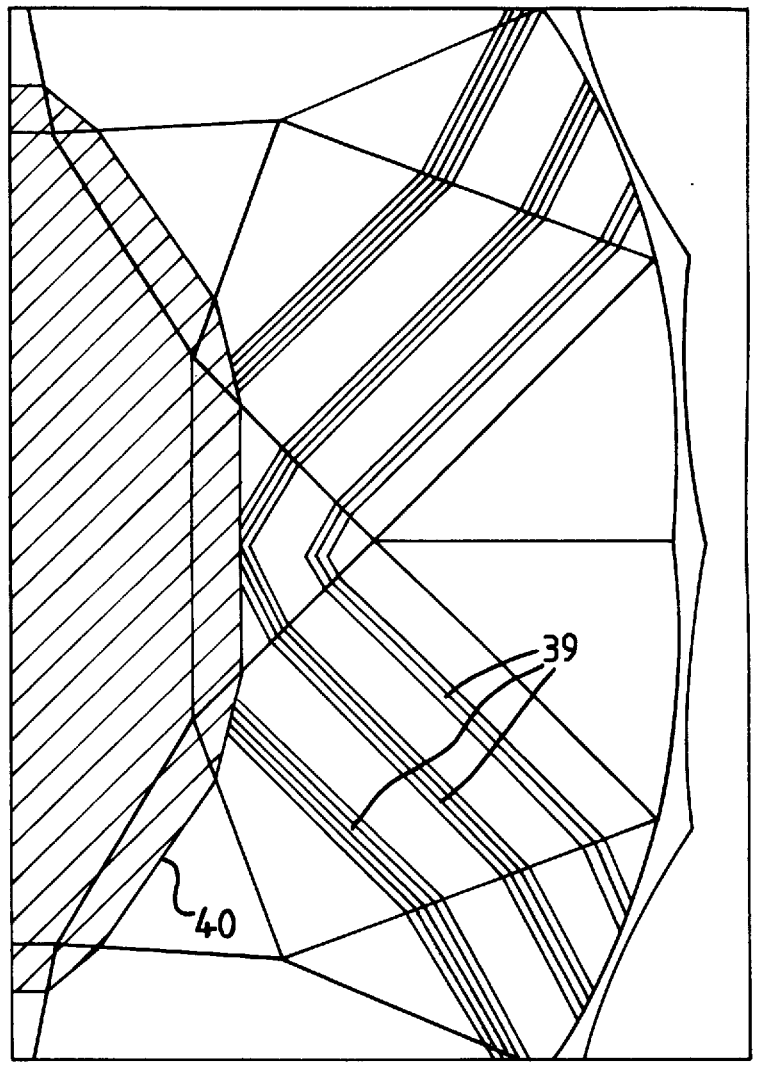
FIG. 7 is a diagrammatic representation, corresponding to FIGS. 3a, 4a, 5a and 6a, but showing the major features of a natural diamond having a surface deposition of synthetic diamond.

FIG. 7 shows the pattern on the image of a circular brilliant-cut natural diamond to the table of which has been applied a vapor deposition layer prior to polishing; only part of the stone is shown. The crown facets in the center of the field of view lie approximately in the focal plane of the microscope. FIG. 7 shows growth bands 39 in the natural diamond substrate and a distinctly different luminescence 40 from the CVD layer on the table and adjacent parts of the crown facets, the luminescence being different in intensity and/or color.

The illuminating ultraviolet radiation is subsequently cut off so that fluorescence (which forms the bulk of the ultraviolet photoluminescence) ceases; any phosphorescence will be revealed and can be observed by eye or using the camera or image recorder 12. In general form, the topographs are similar to those shown in FIGS. 2 to 4a, and the shape of the sectors is the same; however with some diamonds, the presence of individual sectors is accentuated because phosphorescing sectors stand out more clearly against a non-phosphorescing background. The irradiation can be terminated by using a flash lamp for the source 5 or by interposing a shutter 41 in the light path. Whatever means are used for terminating the irradiation, it should be such that the irradiation can be swiftly terminated, e.g. by switching off the power supply 6 or dropping the shutter 41.

* * *

The present invention has been described above purely by way of example, and modifications may be made within the invention.

We claim:

1. A method of examining a diamond having a surface region to determine whether the diamond is a natural diamond or a synthetic diamond, comprising:

irradiating a surface of a diamond with ultraviolet radiation which is preponderantly of a wavelength of less than 225 nm so that preponderantly only the surface region of the diamond is irradiated and so that luminescence emitted by regions of the diamond which are deeper than the surface is insufficient to render indistinct the luminescence produced by the surface; region, whereby the luminescence produced by the surface region forms a luminescence pattern;

providing an image of said luminescence pattern; and observing said image and determining therefrom whether the diamond is natural or synthetic.

2. The method of claim 1, in which fluorescence of the diamond is observed.

3. The method of claim 1, in which the irradiating ultraviolet radiation is terminated and the phosphorescence is observed.

4. The method defined in claim 1, in which irradiating ultraviolet radiation is attenuated to about 13% of its incident intensity within a depth of about 50 $\mu$m below the surface of the diamond.

5. The method defined in claim 1, in which the diamond is observed by eye through magnifying means.

6. The method defined in claim 1, in which a permanent image of said luminescence pattern is formed.

7. The method defined in claim 1, further comprising identifying a said luminescence pattern indicating the disposition of growth sectors in the diamond.

8. The method defined in claim 1, and used to determine whether a diamond has had a layer of synthetic diamond deposited thereon, the method comprising detecting whether zones of superficial synthetic diamond are present by observing said luminescence pattern.

9. Apparatus for examining a diamond having a surface region to determine whether the diamond is a natural diamond or a synthetic diamond, comprising:

means for irradiating a surface of a diamond with ultraviolet radiation which is preponderantly of a wavelength of less than 225 nm so that preponderantly only the surface region of the diamond is irradiated and luminescence emitted by regions of the diamond which are deeper than the surface region are insufficient to render indistinct the luminescence produced by the surface region, whereby the luminescence produced by the surface region forms a luminescence pattern; and means for forming an image of said luminescence pattern, whereby said image can be observed and it can be determined therefrom whether said diamond is natural or synthetic.

10. The apparatus of claim 9, wherein mounting means are provided for mounting the diamond in a viewing zone, and the means for irradiating the surface of the diamond with radiation comprise an illumination source, a lens system and a filter, to pass only a given band of radiation.

11. The apparatus of claim 10, wherein a steerable mirror is provided to direct the irradiating radiation onto the diamond.

12. The apparatus of claim 10, wherein a reflection filter is provided to direct the irradiating radiation onto the diamond.

13. The apparatus defined in claim 9, and comprising image forming means including an image recorder.

14. The apparatus defined in claim 9, and including means for terminating the irradiating ultraviolet radiation and means for observing phosphorescence when the irradiating ultraviolet radiation has been terminated.

15. The apparatus defined in claim 9, and further comprising means for terminating the irradiating ultraviolet radiation and subsequently observing phosphorescence.

16. The apparatus defined in claim 9, wherein said irradiating means irradiates ultraviolet which is attenuated to about 13% of its incident intensity within a depth of about 50 $\mu$m below the surface of the diamond.

17. The apparatus defined in claim 9, wherein said image forming means comprises magnifying means for observation of the diamond by eye.

* * * * *